United States Patent [19]
Xie et al.

[11] Patent Number: 5,817,902
[45] Date of Patent: Oct. 6, 1998

[54] PROCESS FOR PREPARING α-OLEFINS

[75] Inventors: Minghe Xie; Anshun Sun; Daohua Jiang; Jiabo Qu; Qian Chen; Weibin Li; Zongsheng Yuan; Chunmei Yu; Xixia Song; Shubao Wan; Zhengnian Luo; Fengrong Wang; Qun Xu; Shulan Wang; Yingjie Feng; Yongchen Sun, all of Heilongjian Province, China

[73] Assignees: China Petro-Chemical Corporation; Daqing Petrochemical Works; China Petrochemical Corporation, all of Beijing, Switzerland

[21] Appl. No.: 747,517

[22] Filed: Nov. 12, 1996

[30] Foreign Application Priority Data

Nov. 15, 1995 [CN] China .............. 95 1 17459.2

[51] Int. Cl.[6] ............................................. C07C 2/88
[52] U.S. Cl. ........................ 585/328; 585/502; 585/510; 585/517; 585/522; 585/637
[58] Field of Search .................... 585/328, 502, 585/522

[56] References Cited

U.S. PATENT DOCUMENTS

| | | | |
|---|---|---|---|
| 4,037,825 | 7/1977 | Burgert | 259/4 R |
| 4,314,090 | 2/1982 | Shewbart et al. | 585/328 |
| 4,380,684 | 4/1983 | Fowler et al. | 585/328 |
| 4,918,254 | 4/1990 | Diefenbach et al. | 585/328 |
| 4,935,569 | 6/1990 | Harkins et al. | 585/328 |
| 5,157,190 | 10/1992 | Lin et al. | 585/572 |
| 5,403,942 | 4/1995 | Becker et al. | 556/175 |
| 5,498,735 | 3/1996 | Takeuchi et al. | 556/187 |
| 5,518,932 | 5/1996 | Gallant et al. | 585/328 |
| 5,536,859 | 7/1996 | Lin et al. | 556/190 |

*Primary Examiner*—Ellen M. McAvoy
*Attorney, Agent, or Firm*—Burns, Doane, Swecker & Mathis LLP

[57] ABSTRACT

The invention provides a process for making α-olefins. In the chain growth reaction step of the process a jet loop reactor is used to fully use high pressure ethylene, and two or more stages of the chain growth reaction is used to raise the selectivity of $C_{6-10}$ olefins.

11 Claims, 2 Drawing Sheets

PROCESS FOR PREPARING α-OLEFINS

FIELD OF INVENTION

This invention relates to a process for preparing α-olefins, especially an improvement of a process for preparing low carbon α-olefins with ethylene oligomerization in presence of alkyl aluminium catalyst.

BACKGROUND OF THE INVENTION

The two-step process with ethylene oligomerization producing α-olefins has been reported in many documents. The first step is that ethylene and a low molecular weight trialkyl aluminum react in a chain growth reaction zone; and the second step is that low carbon α-olefin is used to replace long chain alkyl of trialkyl aluminum after chain growth so that the desired α-olefins are obtained.

U.S. Pat. No. 4,314,090 has disclosed a process for making $C_{4-10}$ α-olefins wherein a coil reactor is used as a chain growth reactor, and only when mole ratio of ethylene to alkyl moiety of trialkyl aluminium is 10:1 can good chain growth results be realized. By this technology chain growth reaction needs excessive high pressure ethylene and the unreacted ethylene gas is vented, and thus high pressure ethylene can not be sufficiently used. Otherwise, the chain growth reaction of the process is carried out in one stage and the distributions of the replaced product olefins are wider: butene-1 about 30.0%, hexene-1 about 30.0% and octene-1 about 30% with low total selectivity of hexene-1+octene-1.

U.S. Pat. No. 4,380,684 has also disclosed a process for making $C_{4-10}$ α-olefins using a still-type reactor with external circulation. A high pressure ethylene is fed to the reactor and the unreacted ethylene is depressurized as a replacement agent. The purpose of the external circulation is to remove the heat from the reactor and maintain a substantially constant temperature therein. The process has not resolved thoroughly the use of high pressure ethylene as the energy consumption is too high by using high pressure ethylene as a replacement agent after depressurization. Similarly, the chain growth reaction of the process is carried out in one stage too, and the distribution of α-olefins after replacement is as follows: butene-1 about 15%, hexene-1 about 60% and octene-1 about 15%. From this it can be seen that the selectivity of valuable hexene-1 and octene-1 is also low.

There have been many disclosures in prior art with respect to use of a jet loop reactor in chemical process.

U.S. Pat. No. 4,037,825 describes a loop-type reactor with a reactor housing having inlet means at one end and outlet means at the opposite end. Inside the reactor there is a guide tube arranged in the direction of the axis of the inlet means. The inner wall of the reactor is so shaped that the introduced reactants flow through the tube in one direction and are then directed to flow back in the opposite direction through a mixing chamber defined between the outer tube surface and the inner reactor wall. The reactor having such a structure can result in fully mixing the reactant flow and/or bringing about an optimum chemical reaction therein. Meanwhile, the reactor is also focused on smoothing out any thermal gradients induced by any exothermic nature of the polymerization reaction. However, the patent has just disclosed use in a general chemical process.

U.S. Pat. No. 5,403,942 relates to a process for the preparation of aluminoxanes by addition of water to a solution of trialkyl aluminum in an inert solvent, characterized in that the water required for the reaction is metered via a mixing nozzle into a static mixer, in particular a jet loop reactor.

U.S. Pat. No. 4,538,018 discloses a method for dimerizing olefins in a reactor system wherein the reactor may be a loop reactor. However, the method refers to pre-conditioning the walls of an olefin dimerization reactor and starting a dimerization process. Using a loop reactor in the method is optional rather than mandatory. As described in column 2, lines 58–60, "The dimerization of the olefinic feed can take place in any suitable reactor system, e.g., a loop reactor or stirred-tank reactor".

Therefore, it is an object of this invention to provide a process for making α-olefins wherein a jet loop reactor with external circulation is used in a chain growth reaction zone so as to fully use the high pressure ethylene.

It is a second object of this invention to provide a process for making α-olefins wherein multiple stages connected in serial flow are used in a chain growth reaction zone so as to achieve adjustability of the distribution ratio of the object products—higher carbon olefins, especially to raise the total selectivity of hexene-1 and octene-1 or that of $C_{6-10}$ olefins.

SUMMARY OF THE INVENTION

In view of the above, firstly the present invention is directed to a process for making α-olefins wherein ethylene and a low molecular weight trialkyl aluminum solution are fed into a chain growth reactor zone operated under chain growth reaction conditions to provide a higher molecular weight trialkyl aluminum, wherein at least a portion of the resulting higher molecular weight trialkyl aluminum-containing effluent stream is conveyed from the chain growth reactor zone into a replacement reactor zone; wherein the alkyl moieties of the higher molecular weight trialkyl aluminum react with a replacement agent comprising ethylene, a low carbon α-olefin, or a mixture thereof in the replacement reactor zone to produce product higher carbon α-olefines and the low melecular weight trialkyl aluminum; and wherein the products of the replacement reaction zone are conveyed to a separation system to recover the desired higher carbon α-olefins and a low molecular weight trialkyl aluminum solution suitable for recycling to the chain growth reaction zone.

The improvement of the process comprises using a jet loop reactor with external effluent circulation in the chain growth reactor zone such that at least a portion of the effluent stream withdrawn from the jet loop reactor, after compression, is returned to the reactor and jetted off through a first liquid nozzle mounted in the inlet of the reactor thereby to entrain ethylene gas within the reactor together with the liquid jet flow and to eject the resulting liquid-gas mixture from a secondary nozzle to form an internal circulation of the liquid-gas mixture in the reactor until all of the ethylene is reacted out.

Secondly, the present invention is directed to a process for making α-olefins wherein ethylene and a low molecular weight trialkyl aluminum solution are fed into a chain growth reactor zone operated under chain growth reaction conditions to provide a higher molecular weight trialkyl aluminum, wherein at least a portion of the resulting higher molecular weight trialkyl aluminum-containing effluent stream is conveyed from the chain growth reactor zone into a replacement reactor zone; wherein the alkyl moieties of the higher molecular weight trialkyl aluminum react with a replacement agent comprising ethylene, a low carbon α-olefin, or a mixture thereof in the replacement reactor zone to produce product higher carbon α-olefines and low molecular weight trialkyl aluminum; and wherein the products of the replacement reaction zone are conveyed to a separation system to recover the desired higher carbon α-olefins and a low molecular weight trialkyl aluminum solution suitable for recycling to the chain growth reaction zone.

The improvement of the process is in that the chain growth reaction zone comprises multiple stages connected in serial flow wherein ethylene is fed into each stage reactor simultaneously, and a portion of the effluent stream from each stage reactor flows to the next stage reactor in sequence with at least a portion of the effluent stream from the last stage reactor being conveyed to the replacement reaction zone.

Figure 1:
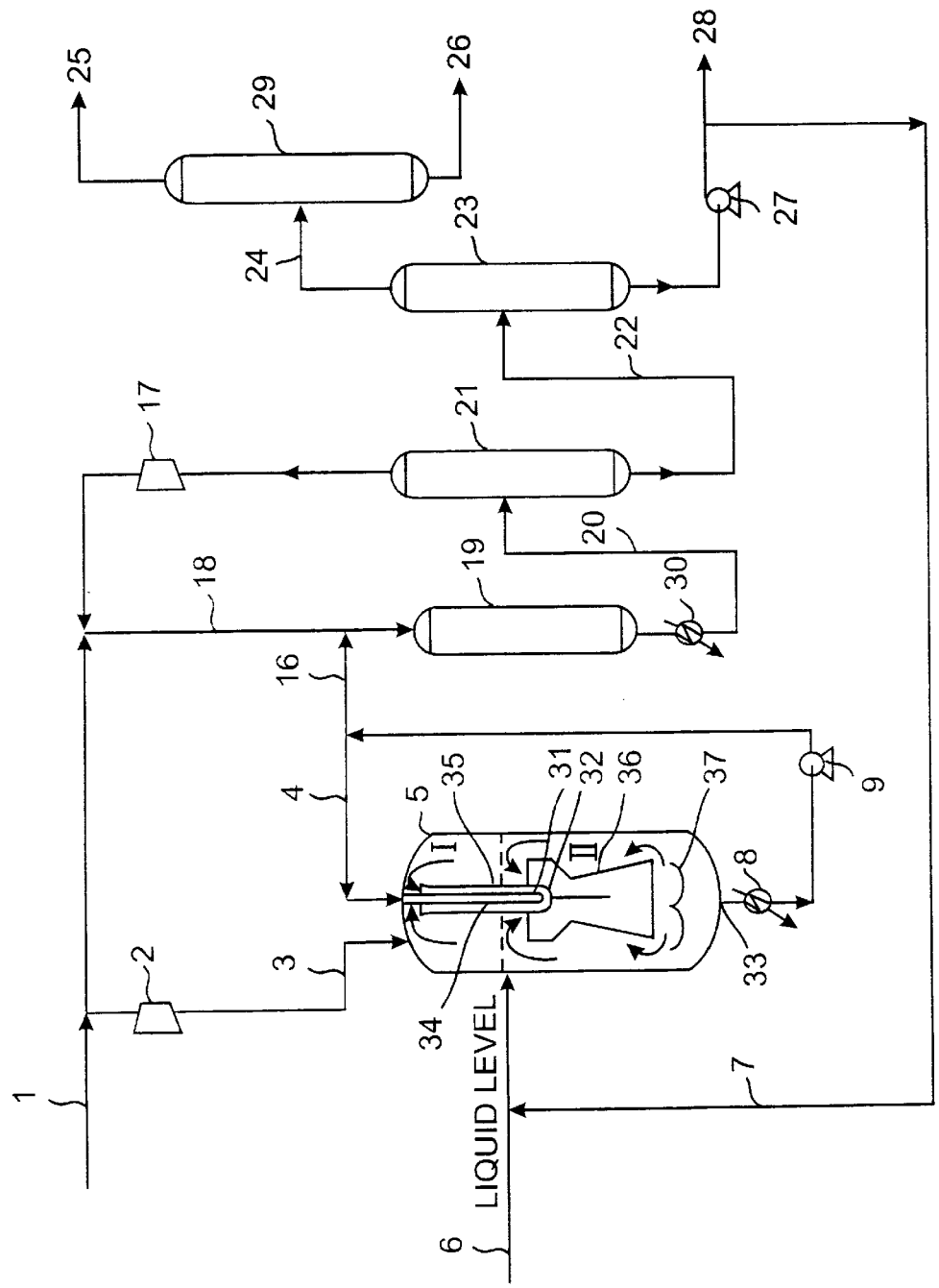
FIG. 1 is a schematic flow diagram of an alpha-olefin preparation process using a jet loop reactor with external effluent circulation in chain growth reaction zone.

The meaning of the reference signs in the drawings is as follows:

1-Ethylene feed line after purification
2-Ethylene compressor
3-Ethylene feed line of the 1st stage chain growth reactor
4-External circulating line for the stream at the bottom of the 1st stage chain growth reactor going back to the reactor
5-The 1st stage chain growth reactor
6-Feed line of alkyl aluminium solution
7-Feed line for the reused alkyl aluminium entering the 1st stage reactor
8, 14 and 30-Coolers
9 and 15-Recirculating pumps
10-Alkyl aluminium solution feed line for the 2nd stage reactor
11-The 2nd stage chain growth reactor
12-Ethylene feed line for the 2nd stage chain growth reactor
13-External circulating line for alkyl aluminium solution at the bottom of the 2nd stage chain growth reactor
16-Alkyl aluminium solution after chain growth
17-$C_{2-4}$ recirculating compressor
18-Feed line for replacement agent
19-Replacement reactor
20-Feed line for $C_{2-4}$ separator
21-$C_{2-4}$ separator
22-Feed line for $C_{6-8}$ separator
23-$C_{6-8}$ separator
24-Feed line for hexene-1 separator
25-Hexene-1
26-Octene-1
27-Reused alkyl aluminum recirculating pump
28-Line for handling periodically high carbon α-olefins (or for further separating and recovering $C_8^+$olefins)
29-Hexene-1 separator
31-First liquid nozzle
32-Secondary nozzle
33-Outlet at the bottom of a jet loop reactor
34-Liquid guide tube
35-Gas guide tube
36-Gas/Liquid guide tube
37-W block-off plate

DETAILED DESCRIPTION OF THE INVENTION

According to the present invention, now referring to FIG. 1 the process for making α-olefins using a jet loop reactor as chain growth reactor is schematically illustrated. Ethylene feed gas from which water and oxygen have been removed enters the jet loop reactor 5 from line 1 via compressor 2. Fresh low molecular weight trialkyl aluminium solution 6 and reused alkyl aluminium solution 7 together enter the reactor 5. In the reactor 5 ethylene and trialkyl aluminium solution react to form chain-grown trialkyl aluminium liquid stream. The stream flows down along the gas/liquid guide tube 36 and unreacted ethylene gas therein is hampered by W block-off plate 37 mounted at the bottom of the reactor. The liquid stream is drawn out from the outlet 33 and divided into two parts after passing through a pump 9 via a cooler 8. One part of the bottom stream goes back to the reactor 5 via line 4 to complete the external recirculation. The recirculated liquid stream is jetted off through a first liquid nozzle 31 at the end of the liquid guide tube 34 mounted in the inlet of the reactor thereby to entrain ethylene gas within the reactor together with the liquid jet flow to enter the gas guide tube 35 and to eject the resulting liquid-gas mixture from a secondary nozzle 32 to form gas/liquid mixture stream in the tube 35. The mixture stream is drawn out from the lower outlet of the tube 36 and returned to the upper inlet of the tube 36 via an annular space between an external wall of the guide tube 36 and an internal wall of the reactor 5 to form a loop flow of internal recirculation (as shown by II). The unreacted etheylene gas gets into a space above a liquid level in the reactor and is recirculated to the reactant stream via the gas guide tube 35 (as shown by I). Such moving back and forth keeps on until all of the ethylene is reacted out. Another part of the bottom stream from the reactor 5 enters a replacement reactor 19 via the line 16. The replacement agent of ethylene and/or butene-1 from line 1 and compressor 17 also enters the replacement reactor 19 via line 18. The bottom stream of the reactor 19 after cooling is fed to $C_{2-4}$ olefins separator 21 via line 20. The overhead stream of the separator 21 is drawn out therefrom and returned to the replacement reactor 19 via the compressor 17. The effluent stream ($C_{6-8}$ olefins and low molecular weight trialkyl aluminium) from the bottom of the separator 21 is fed to the separator 23 via line 22. The overhead stream of $C_{6-8}$ olefins enters a separator 29 via line 24 and are separated to produce hexene-1 and octene-1, while the bottom stream of trialkyl aluminium solution is pumped by the pump 27 and returned to the chain growth reactor 5 to reuse. A part of reused trialkyl aluminium solution is periodically fed to line 28 where high carbon α-olefin is removed (or $C_8^+$olefins are further recovered).

The velocity at the first liquid nozzle of the returned portion of the effluent stream from the reactor 5 is in the range of 10–100 m/s, preferably 30–50 m/s. The chain growth reaction conditions include a temperature in the range of 100°–140° C., preferably 110°–120° C.; a pressure in the range of 2.0–10 MPa (G), preferably 3.5–6.0 MPa (G); and a residence time in the range of 10–60 min, preferably 25–30 min.

According to the present invention, in the process for making α-olefins the multiple stages connected in serial flow are used in a chain growth reaction zone, preferably two stages, to achieve the adjustability of the distribution of higher carbon α-olefins and to produce $C_{6-12}$ olefins, especially $C_{6-8}$ olefins, with high selectivity. Now referring to FIG. 2, the two stages technology is schematically illustrated as follows:

Ethylene from line 1 via compressor 2, from which water and oxygen are removed, simultaneously enters the first stage chain growth reactor 5 and the second reactor 11 through lines 3 and 12 respectively. The fresh trialkyl aluminium solution via line 6 and the reused trialkyl aluminium solution via line 7 enter the first stage chain growth reactor 5 where ethylene and trialkyl aluminium solution react to proceed to a preliminary chain growth reaction. The bottom stream from the reactor 5 flows through cooler 8 and pump 9 and preferably is divided into two parts. One part of the stream is returned to the first stage reactor 5 to form an external recirculation, while another part of the stream is fed to the second stage reactor 11 via line 10 and reacted with ethylene to proceed to further chain growth reaction. The bottom stream of the reactor 11 after passing through cooler 14 is pumped down by pump 15 and preferably is divided into two parts. One part of the stream is returned to the second stage reactor 11 to form an external recirculation, while another part of the stream is fed to a replacement reactor 21 via line 16 where it together with the replacement agent proceeds to replacement reaction, which is ethylene and/or butene-1 from line 1 and compressor 17. Afterwards, the separation and the recovery of hexene-1 and octene-1 and the further recovery of $C_8^+$ olefins and the reuse of the low molecular weight trialkyl aluminium are as above-stated.

The reactor used in each stage of the multiple stages technology can be selected from the group consisting of a jet loop reactor, tank type reactor and reactor of other type, preferably the reactor used in at least one stage is a jet loop reactor, in which the velocity of the first liquid nozzle is in the range of 10–100 m/s, preferably 30–50 m/s.

The number of stages to be chosen will depend on the desired products and their distribution. For example, to obtain high selectivity of $C_6 + C_8$ olefins, two-stage technology is preferable to be used. In this case, preferable reaction conditions of the first and the second stages are as follows respectively:

For the first stage: the temperature is in the range of 70°–110° C., preferably 80°–100° C.; the pressure is in the range of 2.0–4.5 MPa (G), preferably 3.0–4.0 MPa (G); and the residence time is in the range of 5–30 min, preferably 10–20 min.

For the second stage: the temperature is in the range of 100°–140° C., preferably 110°–120° C., the pressure is in the range of 3.0–6.0 MPa (G), preferably 4.0–5.0 MPa (G), and the residence time is in the range of 10–40 min, preferably 15–25 min.

According to the present invention the process for making α-olefins has two advantages and good effects. Using a jet loop reactor as chain growth reactor can make full use of high pressure ethylene, effectively reduce the product cost and the equipment investment and be beneficial to the industrialized production. And, using two-stage chain growth reaction can obviously increase the total selectivity of hexene-1 and octene-1 or that of $C_{6-10}$ olefins, their total selectivity being more 90%.

The invention is further illustrated by the following examples which should not be regarded as more limiting than the appended claims.

EXAMPLES

Examples 1–8

The process for making α-olefins using a jet loop reactor as chain growth reactor is carried out as shown in the schematic diagram of FIG. 1. The chain growth agent is made of 260 g triethyl aluminium, 300 g tributyl aluminium and 540 g n-tridecane. The reused amount of trialkyl aluminium solution is 1.6 kg/h (except that the reused amount is 22.0 kg/h for example 8). Ethylene passes through the chain growth reactor continuously so as to keep the reactor at a constant pressure.

Table 1 lists the velocity of the first liquid nozzle and other reaction conditions, and the results about ethylene use-up percent.

TABLE 1

| Example No. | 1 | 2 | 3 | 4 | 5 | 6 | 7 | 8 |
|---|---|---|---|---|---|---|---|---|
| velocity of nozzle (m/s) | 25 | 10 | 30 | 50 | 65 | 75 | 85 | 100 |
| temperature (°C.) | 115 | 120 | 120 | 100 | 110 | 120 | 110 | 140 |
| pressure (MPa) | 5.5 | 4.5 | 2.0 | 4.0 | 10 | 3.8 | 5.5 | 6.0 |
| residence time (min) | 40 | 40 | 25 | 35 | 35 | 25 | 40 | 60 |
| ethylene use-up (%)* | 100 | 100 | 100 | 100 | 100 | 100 | 100 | 100 |

*Ethylene has been reacted out, except that very little amount of ethylene is dissolved in the trialkyl aluminium solution.

Examples 9–16

Figure 2:
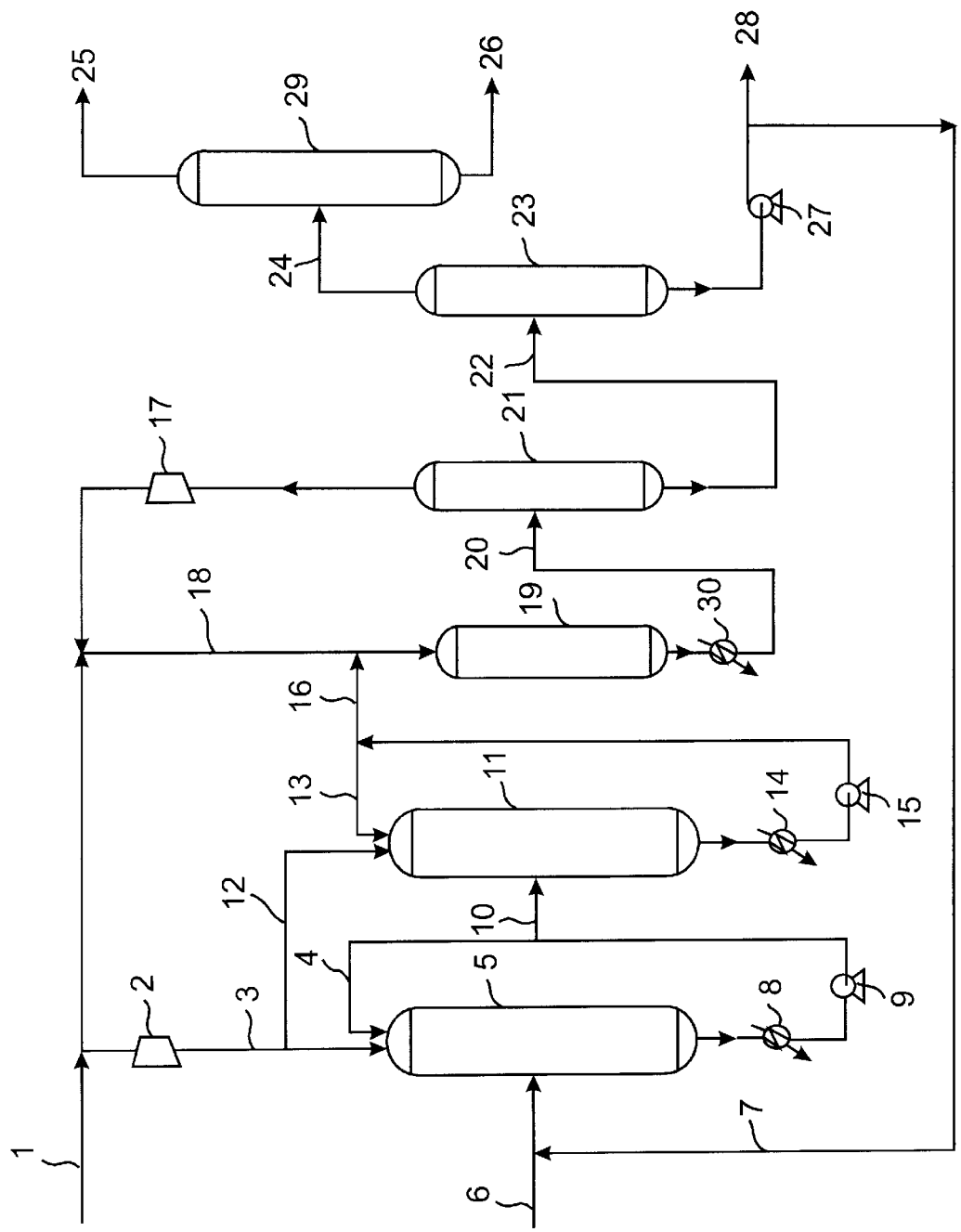
FIG. 2 is a schematic flow diagram of an alpha-olefin preparation process using two-stage chain growth reaction.

The process for making α-olefins using two-stage chain growth reaction is carried out as shown in the schematic diagram of FIG. 2. The chain growth agent is made of 260 g triethyl aluminium, 300 g tributyl aluminium and 540 g n-tridecane. Ethylene passes through the first and the second stage chain growth reactors continuously so as to keep the reactors at a constant pressure. The reused amount of the trialkyl aluminium solution is 1.6 kg/h. In both the first and the second stage reactor a jet loop reactor is used with the velocity of the nozzle being 10–100 m/s. All the returned butene-1 mixes with ethylene as replacement agent. Table 2 lists the chain growth reaction conditions of the first and the second stage, the replacement reaction conditions and the ratio of replacement agent to the alkyl moieties of trialkyl aluminium. The results about the distribution of the products are also listed in Table 2. From Table 2, it can be seen that the total selectivity of hexene-1 and octene-1 all is more than 90%.

TABLE 2

| | Example No. | 9 | 10 | 11 | 12 | 13 | 14 | 15 | 16 |
|---|---|---|---|---|---|---|---|---|---|
| First stage | temperature(°C.) | 90 | 90 | 80 | 85 | 100 | 170 | 100 | 100 |
| | pressure(MPa) | 3.0 | 3.5 | 2.8 | 3.0 | 2.8 | 3.5 | 4.0 | 3.5 |
| | residence time(min) | 15 | 20 | 5 | 18 | 30 | 20 | 12 | 20 |
| Second | temperature(°C.) | 120 | 100 | 110 | 115 | 120 | 112 | 120 | 140 |

TABLE 2-continued

| Example No. | | 9 | 10 | 11 | 12 | 13 | 14 | 15 | 16 |
|---|---|---|---|---|---|---|---|---|---|
| stage | pressure(MPa) | 4.2 | 4.5 | 4.5 | 2.0 | 5.0 | 6.0 | 4.0 | 3.5 |
| | residence time(min) | 20 | 30 | 10 | 25 | 40 | 20 | 20 | 20 |
| replacement | temperature(°C.) | 267 | 265 | 300 | 270 | 200 | 267 | 270 | 267 |
| | pressure(MPa) | 0.8 | 0.75 | 0.10 | 1.0 | 0.8 | 0.75 | 0.80 | 0.75 |
| reaction | residence time(min) | 0.4 | 0.4 | 0.1 | 0.5 | 0.4 | 0.4 | 2.0 | 3.0 |
| mole ratio of replacement agent to alkyl of trialkyl aluminium | | 15:1 | 20:1 | 25:1 | 15:1 | 18:1 | 10:1 | 15:1 | 20:1 |
| distribution (%) | $C_{6-}$ | 64.9 | 60.9 | 59.0 | 66.2 | 62.8 | 55.2 | 56.8 | 58.2 |
| | $C_{8-}$ | 27.3 | 29.3 | 31.2 | 24.9 | 32.5 | 36.3 | 33.5 | 33.3 |
| | $C_{10-}$ | 7.0 | 8.8 | 8.5 | 7.9 | 3.7 | 6.5 | 8.7 | 6.5 |
| | $C_{12-}$ | 0.6 | 0.8 | 1.0 | 0.9 | 0.8 | 1.4 | 0.8 | 1.4 |

Examples 17–19

The operation procedure is carried out as described in Examples 9–16 except for the change of the composition and the proportion of the chain growth agent (moreover, the suitable composition can be also obtained by adjusting the proportion in the mixture of the replacement agents). In order to increase the relative yield of $C_{8-10}$ olefins, for example, to obtain the main product octene-1 and meantime to raise the relative yield of decene-1, the composition and the proportion of the chain growth agent can be adjusted (such as adding trihexyl aluminium), though the total selectivity of hexene-1 and octene-1 is below 90% owing to reduction of the relative yield of hexene-1 (Examples 17–18: the total selectivity of $C_6+C_8$ is 84% but the selectivity of $C_8$ is raised to 44–50%, and the total selectivity of $C_{6-10}$ is 94–96%; Example 19: the total selectivity of $C_6+C_8$ is 70% but the selectivity of $C_8$ is 40%, the selectivity of $C_{10}$ is 20% and the total selectivity of $C_{6-10}$ is 90%). Table 3 lists the composition of the chain growth agent, the first and the second stage reaction conditions and the product distribution.

TABLE 3

| Example No. | 17 | 18 | 19 |
|---|---|---|---|
| composition | | | |
| triethyl aluminium (g) | 450 | 400 | 340 |
| n-tributyl aluminium (g) | 250 | 400 | 660 |
| n-trihexyl aluminium (g) | 150 | 100 | 0 |
| n-tridecane (g) | 250 | 0 | 0 |
| First stage | | | |
| temperature (°C.) | 80 | 80 | 90 |
| pressure (MPa) | 4.0 | 5.0 | 5.5 |
| residence time (min) | 15 | 15 | |
| Second stage | | | |
| temperature (°C.) | 110 | 102 | 105 |
| pressure (MPa) | 7.0 | 7.0 | 8.5 |
| residence time (min) | 20 | 20 | 20 |
| distribution (%) | | | |
| $C_{6-}$ | 40.0 | 38.0 | 30.0 |
| $C_{8-}$ | 44.0 | 46.0 | 40.0 |
| $C_{10-}$ | 10.0 | 12.0 | 20.0 |
| $C_{12-}$ | 4.0 | 3.0 | 7.0 |

We claim:

1. In a process for making α-olefins wherein ethylene and a low molecular weight trialkyl aluminum solution are fed into a chain growth reactor zone operated under chain growth reaction conditions to provide a higher molecular weight trialkyl aluminum, wherein at least a portion of the resulting higher molecular weight trialkyl aluminum-containing effluent stream is conveyed from the chain growth reactor zone into a replacement reactor zone;

wherein the alkyl moieties of the higher molecular weight trialkyl aluminum react with a replacement agent comprising ethylene, a low carbon α-olefin, or a mixture thereof in the replacement reactor zone to produce product higher carbon α-olefines and the low melecular weight trialkyl aluminum;

and wherein the products of the replacement reaction zone are conveyed to a separation system to recover the desired higher carbon α-olefins and a low molecular weight trialkyl aluminum solution suitable for recycling to the chain growth reaction zone;

the improvement which comprises using a jet loop reactor with external effluent circulation in the chain growth reactor zone such that at least a portion of the effluent stream withdrawn from the jet loop reactor, after compression, is returned to the reactor and jetted off through a first liquid nozzle mounted in the inlet of the reactor thereby to entrain ethylene gas within the reactor together with the liquid jet flow and to eject the resulting liquid-gas mixture from a secondary nozzle to form an internal circulation of the liquid-gas mixture in the reactor until all of the ethylene is reacted out.

2. The improved process according to claim 1, wherein the velocity of the returned portion of the effluent stream in the first liquid nozzle is in the range of 10–100 m/s.

3. The improved process according to claim 2, wherein the velocity of the returned portion of the effluent stream in the first liquid nozzle is in the range of 30–50 m/s.

4. The improved process according to claim 1, wherein the chain growth reaction conditions include a temperature in the range of 100°–140° C., a pressure in the range of 2.0–10 MPa (G) and a residence time in the range of 10–60 min.

5. The improved process according to claim 1 wherein the chain growth reaction conditions include a temperature in the range of 110°–120° C., a pressure in the range of 3.5–6.0 MPa (G) and a residence time in the range of 25–30 min.

6. In a process for making α-olefins, wherein ethylene and a low molecular weight trialkyl aluminum solution are fed into a chain growth reactor zone operated under chain growth reaction conditions to provide a higher molecular weight trialkyl aluminum, wherein at least a portion of the resulting higher molecular weight trialkyl aluminum-containing effluent stream is conveyed from the chain growth reactor zone into a replacement reactor zone;

wherein the alkyl moieties of the higher molecular weight trialkyl aluminum react with a replacement agent comprising ethylene, a low carbon α-olefin, or a mixture thereof in the replacement reactor zone to produce product higher carbon α-olefines and the low molecular weight trialkyl aluminum;

and wherein the products of the replacement reaction zone are conveyed to a separation system to recover the desired higher carbon α-olefins and a low molecular weight trialkyl aluminum solution suitable for recycling to the chain growth reaction zone;

the improvement which is in that the chain growth reaction zone comprises multiple stages connected in serial flow wherein ethylene is fed into each stage reactor simultaneously, and a portion of the effluent stream from each stage flows to the next stage in sequence with at least a portion of the effluent stream from the last stage being conveyed to the replacement reaction zone.

7. The improved process according to claim 6, wherein at least a portion of the effluent stream from each chain growth reactor stage is returned to the inlet of said chain growth reactor stage respectively to form an external circulation flow pattern around each stage.

8. The improved process according to claim 6, wherein the reactor used in each stage is selected from the group consisting of a jet loop reactor, tank type reactor and other reactor.

9. The improved process according to claim 8, wherein the reactor used in at least one stage is a jet loop reactor.

10. The improved process according to claim 6 wherein two stages are utilized and in the first stage the reaction temperature is in the range of 70°–110° C., the reaction pressure in the range of 2.0–4.5 MPa (G), and the residence time in the range of 5–30 min., and in the second stage the reaction temperature is in the range of 100°–140° C., the reaction pressure in the range of 3.0–6.0 MPa (G) and the residence time in the range of 10–40 min.

11. The improved process according to claim 10, wherein two stages are utilized and in the first stage the reaction temperature is in the range of 80°–100° C., the reaction pressure in the range of 3.0–4.0 MPa (G) and the residence time in the range of 10–20 min; and in the second stage the reaction temperature is in the range of 110°–120° C., the reaction pressure in the range of 4.0–5.0 MPa (G) and the residence time in the range of 15–25 min.

* * * * *